United States Patent [19]

Sirrenberg et al.

[11] 4,005,223
[45] Jan. 25, 1977

[54] INSECTICIDAL 2-CHLORO-4'-[N-(N'-BENZOYL)-UREIDO]-DIPHENYL ETHERS

[75] Inventors: Wilhelm Sirrenberg, Sprockhoevel; Jürgen Schramm, Dormagen; Erich Klauke, Odenthal; Ingeborg Hammann, Cologne, all of Germany

[73] Assignee: Bayer Aktiengesellschaft, Leverkusen, Germany

[22] Filed: Feb. 3, 1976

[21] Appl. No.: 654,835

[30] Foreign Application Priority Data

| Feb. 6, 1975 | Germany | 2504982 |
| Feb. 6, 1975 | Germany | 2504984 |
| June 28, 1975 | Germany | 2528917 |
| Aug. 22, 1975 | Germany | 2537413 |

[52] U.S. Cl. ............................ 424/322; 260/553 A
[51] Int. Cl.² ..................................... A01N 9/20
[58] Field of Search ............... 260/553 A; 424/322

[56] References Cited

OTHER PUBLICATIONS

Chemical Abstracts 76; 85578m (1972).

*Primary Examiner*—Leonard Schenkman
*Attorney, Agent, or Firm*—Burgess, Dinklage & Sprung

[57] ABSTRACT

2-Chloro-4'-[N-(N'-benzoyl)-ureido]-diphenyl ethers of the formula

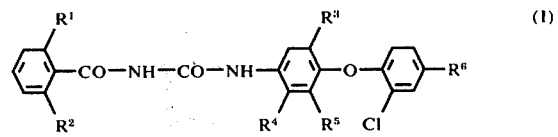

in which
R¹ is fluorine, chlorine, bromine or methyl,
R² is hydrogen, fluorine or chlorine,
R³ is hydrogen or chlorine,
R⁴ is hydrogen, chlorine or methyl,
R⁵ is hydrogen or chlorine, and
R⁶ is nitro or trifluoromethyl.

which possess insecticidal properties.

12 Claims, No Drawings

INSECTICIDAL 2-CHLORO-4'-[N-(N'-BENZOYL)-UREIDO]-DIPHENYL ETHERS

The present invention relates to and has for its objects the provision of particular new 2-chloro-4'-[N-(N'-benzoyl)-ureido]-diphenyl ethers, which possess insecticidal properties, active compositions in the form of mixtures of such compounds with solid and liquid dispersible carrier vehicles, and methods for producing such compounds and for using such compounds in a new way especially for combating pests, e.g. insects, with other and further objects becoming apparent from a study of the within specification and accompanying examples.

It is known from German Published Specification DOS 2,123,236 that certain benzoylureas, such as, for example, N-(2,6-dichlorobenzoyl)-N'-(4-chlorophenyl-(Compound A) and -3,4-dichlorophenyl)-urea (Compound B), possess insecticidal properties.

The present invention provides the benzoylureidodiphenyl ethers of the general formula

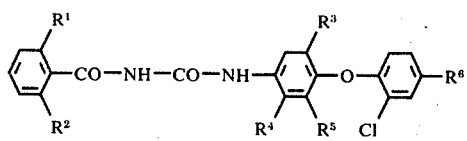

in which
R$^1$ is fluorine, chlorine, bromine or methyl,
R$^2$ is hydrogen, fluorine or chlorine,
R$^3$ is hydrogen or chlorine,
R$^4$ is hydrogen, chlorine or methyl,
R$^5$ is hydrogen or chlorine, and
R$^6$ is nitro or trifluoromethyl.

A preferred class of benzoylureidodiphenyl ethers of the formula (I) are those in which R$^1$ is chlorine or fluorine, R$^2$ is hydrogen, chlorine or fluorine, R$^3$, R$^4$ and R$^5$ are each hydrogen, and R$^6$ represents trifluoromethyl.

Another preferred class of benzoylureidodiphenyl ethers of the formula (I) are those in which R$^1$ is chlorine, fluorine or methyl, R$^2$ is hydrogen, chlorine or fluorine, R$^3$ is hydrogen or chlorine, R$^4$ is hydrogen, R$^5$ is hydrogen or chlorine, and R$^6$ is nitro.

A further preferred class of benzoylureidodiphenyl ethers of the formula (I) are those in which R$^1$ is chlorine, fluorine or bromine, R$^2$ is hydrogen or fluorine, R$^3$ is hydrogen, R$^4$ is methyl or chlorine, R$^5$ is hydrogen and R$^6$ represents nitro.

Surprisingly, the benzoylureido-diphenyl ethers according to the invention have a substantially better insecticidal action than the nearest compounds of analogous structure and of the same type of action previously known from the state of the art. The compounds according to the invention thus represent a genuine enrichment of the art.

The present invention also provides a process for the preparation of a benzoylureidodiphenyl ether of the formula (I) in which
(a) a phenoxyaniline of the general formula

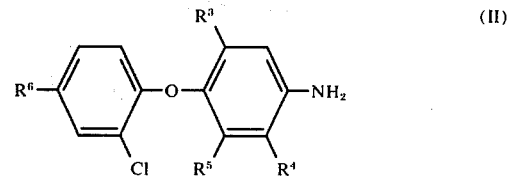

is reacted with a benzoylisocyanate of the general formula

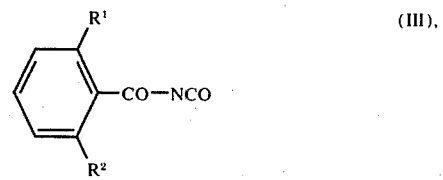

in which formulas
R$^1$ to R$^6$ have the above-mentioned meanings,
if appropriate in the presence of a diluent or solvent, or
(b) a 4-isocyanato-diphenyl ether of the general formula

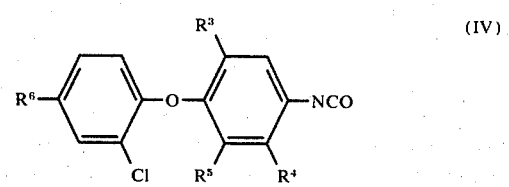

is reacted with a benzamide of the general formula

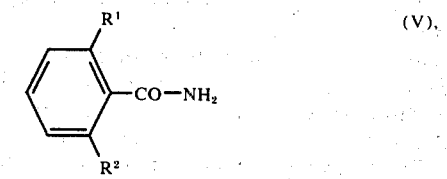

in which formulas
R$^1$ to R$^6$ have the above-mentioned meanings,
if appropriate in the presence of a diluent or solvent.

If, using process variant (a), 4-(2'-chloro-4'-trifluoromethylphenoxy)-aniline and 2-chlorobenzoylisocyanate are used as starting materials and, using process variant (b), 4-(2'-chloro-4'-trifluoromethylphenoxy)-phenylisocyanate and 2,6-difluorobenzamide are used as starting materials, the course of the reactions can be represented by the following equations:

(a)

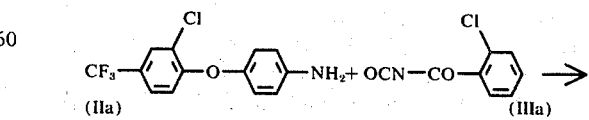

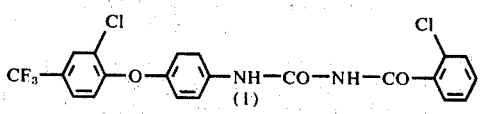

(b)

-continued

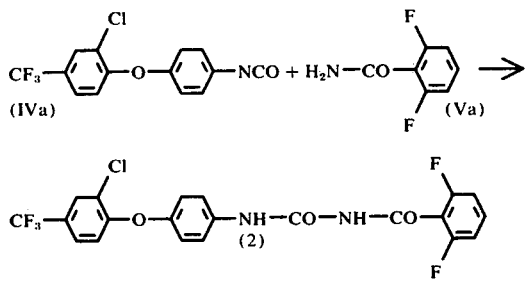

The benzoylisocyanates (III) to be used as starting materials are known from the literature and can be prepared according to generally customary processes (see A. J. Speziale et al., J. Org. Chem. 30 (12), pages 4306–4307 (1965)).

2,6-Difluorobenzamide and the other benzamides (V) are known and can be prepared according to generally customary processes (see Beilsteins Handbuch der organischen Chemie (Beilstein's Handbook of Organic Chemistry), volume 9, page 336). The phenoxyanilines (II) can be prepared according to generally customary processes, for example from alkali metal aminophenolates and 1,2-dichloro-4-trifluoromethylbenzene or aromatic nitrohalogeno compounds such as 1,2-dichloro-4-nitrobenzene in a solvent, for example dimethylsulfoxide (see also Jurgen Schramm et al., Justus Liebigs Annalen der Chemie 1970, 740, 169–179). The amino group can be converted into the isocyanate group in accordance with generally customary processes, for example by reaction with phosgene, whereby the 4-isocyanatodiphenyl ethers of the general formula (IV) are obtained.

The following may be mentioned as examples of the benzoylisocyanates (III) and benzamides (V) to be reacted in accordance with the process: 2-chloro-, 2-fluoro-, 2-bromo-, 2,6-dichloro- or 2,6-difluoro-benzoylisocyanate, and 2-chloro-, 2-fluoro-, 2-bromo-, 2,6-dichloro- or 2,6-difluoro-benzamide.

The following may be mentioned as examples of the phenoxyanilines (II) and 4-isocyanato-diphenyl ethers (IV) to be reacted in accordance with the process: 3-chloro-4-(2'-chloro-4'-nitro-phenoxy)-aniline, 3,5-dichloro-4-(2'-chloro-4'-nitro-phenoxy)-aniline and 4-(2'-chloro-4'-nitro-phenoxy)-aniline, and 2,6-dichloro-4-isocyanato-2'-chloro-4'-nitrodiphenyl ether, 2-chloro-4-isocyanato-2'-chloro-4'-nitrodiphenyl ether and 4-isocyanato-2'-chloro-4'-nitro-diphenyl ether.

The process for the preparation of the benzoylureidodiphenyl ethers according to the invention is preferably carried out in the presence of a suitable solvent or diluent. Practically all inert organic solvents can be used for this purpose, especially aliphatic and aromatic, optionally chlorinated hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and benzonitrile.

The reaction temperature can be varied within a fairly wide range. In general, the reaction is carried out at between 0° and 120° C, preferably at 70° to 85° C.

In general, the reaction is allowed to take place under normal pressure.

Preferably, the reactants are employed in equimolar amounts for carrying out the process. An excess of one or other component produces no significant advantages.

The 4-isocyanato-diphenyl ethers (IV) used in process variant (b) above can be employed as such or, without intermediate isolation, in the form of their reaction mixtures obtained from the reaction of amine with phosgene. This reaction mixture, in one of the above-mentioned solvents, is mixed with a benzamide, for example with 2,6-difluorobenzamide. The reaction is carried out under the desired conditions and the product which separates out is isolated in the usual manner by filtration, washing and, if appropriate, recrystallization.

The compounds are obtained in a crystalline form of sharp melting point.

As has already been mentioned, the benzoylureidodiphenyl ethers according to the invention are distinguished by an excellent insecticidal activity; this is coupled with low toxicity to warm-blooded animals and good toleration by plants.

For this reason, the compounds according to the invention can be employed successfully in plant protection as pesticides against biting and sucking insects.

To the sucking insects there belong, in the main, aphids (Aphididae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrips (Thysanoptera), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly caterpillars (Lepidoptera) such as the diamond-back moth (*Plutella maculipennis*), the gypsy moth (*Lymantria dispar*), the browntail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (Prodenia litura), the ermine moth (*Hyponomeuta padella*), the Mediterranean flour moth (*Ephestia kuhniella*) and greater wax moth (*Galleria mellonella*).

Also to be classed with the biting insects are beetles (Coleoptera), for example the granary weevil (*Sitophilus granarius* = *Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (*Bruchidius* = *Acanthoscelides obtectus*), the leather beetle (*Dermestes frischi*), the khapra beetle (*Trogoderma granarium*), the flour beetle (*Tribolium castaneum*), the northern corn billbug (*Calandra* or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (*Agriotes* spec.) and larvae of the cockchafer (*Melolontha melolontha*); cockroaches, such as the German cockroach (*Blattella germanica*), American cockroach (Periplaneta americana), Madeira cockroach (*Leucophaea* or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, Orthoptera, for example the house cricket (*Gryllus domesticus*); termites such as the eastern subterranean termite (*Reticulitermes flavipes*) and Hymenoptera such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further gnats, for example mosquitoes such as the yellow fever mosquito (*Aedes aegypti*), the northern house mosquito (*Culex pipiens*) and the malaria mosquito (*Anopheles stephensi*).

When applied against pests harmful to health and pests of stored products, particularly flies and mosquitoes, the process products are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides, or acaricides, nematocides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, granules, natural and synthetic materials impregnated with active compound, very fine capsules in polymeric substances and in coating compositions, formulations used with burning equipment such as fumigating cartridges, fumigating cans, fumigating coils and the like, as well as ULV (ultra-low-volume) cold mist and warm mist formulations.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects, which comprises applying to at least one of (a) such insects, and (b) the corresponding habitat thereof, i.e. the locus to be protected, e.g. to a growing crop, to an area where a crop is to be grown, to seed or to a domestic animal, a correspondingly combative or toxic amount, i.e. insecticidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Plutella test

Solvent: 3 parts by weight of dimethylformamide

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamond-back moth (*Plutella maculipennis*).

After the specified periods of time, the degree of destruction was determined as a percentage: 100% means that all the caterpillars were killed whereas 0% means that none of the caterpillars were killed.

The active compounds, the concentrations of the active compounds, the evaluation times and the results can be seen from the following table:

TABLE 1

(insects which damage plants)
Plutella test

| Active compound | | Active compound in % | Degree of destruction in % after 8 days |
|---|---|---|---|
| 2,6-dichloro-Cl-phenyl-CO—NH—CO—NH—phenyl-Cl (known) | (A) | 0.1<br>0.01 | 65<br>0 |
| 2,6-dichloro-Cl-phenyl-CO—NH—CO—NH—2,6-dichloro-Cl-phenyl (known) | (B) | 0.1<br>0.01<br>0.001 | 100<br>100<br>15 |
| 2,6-dichloro-Cl-phenyl-CO—NH—NH—phenyl-O-phenyl-CF₃ (with Cl) | (3) | 0.1<br>0.01<br>0.001 | 100<br>100<br>90 |
| 2,6-difluoro-F-phenyl-CO—NH—CO—NH—phenyl-O-phenyl-CF₃ (with Cl) | (2) | 0.1<br>0.01<br>0.001 | 100<br>100<br>95 |
| 2-CH₃-phenyl-CO—NH—CO—NH—phenyl-O-phenyl-NO₂ (ClCl) | (5) | 0.1<br>0.01<br>0.001 | 100<br>100<br>100 |
| 2-CH₃-phenyl-CO—NH—CO—NH—Cl-phenyl-O-phenyl-NO₂ (ClCl) | (12) | 0.1<br>0.01<br>0.001 | 100<br>100<br>100 |

TABLE 1-continued (insects which damage plants)
*Plutella* test

| Active compound | | Active compound in % | Degree of destruction in % after 8 days |
|---|---|---|---|
| [2-Cl-C$_6$H$_4$-CO-NH-CO-NH-(2,6-Cl$_2$-C$_6$H$_2$)-O-(2-Cl-C$_6$H$_3$)-NO$_2$] | (9) | 0.1<br>0.01<br>0.001 | 100<br>100<br>100 |
| [2-Cl-C$_6$H$_4$-CO-NH-CO-NH-(2,6-Cl$_2$-C$_6$H$_2$)-O-(2-Cl-C$_6$H$_3$)-NO$_2$] | (4) | 0.1<br>0.01<br>0.001 | 100<br>100<br>100 |

EXAMPLE 2

Laphygma test
Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Cotton leaves (*Gossypium hirsutum*) were sprayed with the preparation of the active compound until dew-moist and were then infested with caterpillars of the owlet moth (*Laphygma exigua*).

After the specified periods of time, the destruction in % was determined. 100% means that all the caterpillars had been killed, whereas 0% indicates that no caterpillars had been killed.

The active compounds, the concentrations of the active compound, the evaluation times and the results can be seen from the following table:

Table 2

(insects which damage plants)
*Laphygma* test

| Active compounds | | Active compound concentration in % | Degree of destruction in % after 8 days |
|---|---|---|---|
| 2,6-Cl$_2$-C$_6$H$_3$-CO-NH-CO-NH-(2,4-Cl$_2$-C$_6$H$_3$)-Cl (known) | (B) | 0.001<br>0.0001<br>0.00001 | 100<br>50<br>0 |
| 2-Cl-C$_6$H$_4$-CO-NH-CO-NH-C$_6$H$_4$-O-(3-Cl-C$_6$H$_3$)-CF$_3$ | (1) | 0.001<br>0.0001<br>0.00001 | 100<br>100<br>100 |
| 2,6-Cl$_2$-C$_6$H$_3$-CO-NH-CO-NH-C$_6$H$_4$-O-(3-Cl-C$_6$H$_3$)-CF$_3$ | (3) | 0.001<br>0.0001<br>0.00001 | 100<br>80<br>60 |
| 2,6-F$_2$-C$_6$H$_3$-CO-NH-CO-NH-C$_6$H$_4$-O-(3-Cl-C$_6$H$_3$)-CF$_3$ | (2) | 0.001<br>0.0001<br>0.00001 | 100<br>100<br>95 |
| 2,6-F$_2$-C$_6$H$_3$-CO-NH-CO-NH-(3-CH$_3$-C$_6$H$_3$)-O-(2-Cl-C$_6$H$_3$)-NO$_2$ | (14) | 0.001<br>0.0001<br>0.00001 | 100<br>100<br>70 |

Table 2-continued (insects which damage plants)
*Laphygma* test

| Active compounds | | Active compound concentration in % | Degree of destruction in % after 8 days |
|---|---|---|---|
| 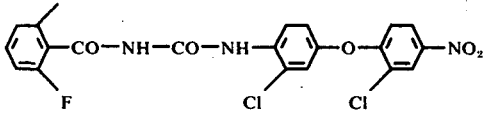 | (15) | 0.001<br>0.0001<br>0.00001 | 100<br>100<br>50 |

EXAMPLE 3

Phaedon larvae test
Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) were sprayed with the preparation of the active compound until dripping wet and were then infested with mustard beetle larvae (*Phaedon cochleariae*).

After the specified periods of time, the degree of destruction was determined in %: 100% means that all beetle larvae had been killed, whereas 0% means that none of the beetle larvae had been killed.

The active compounds, the concentrations of the active compounds, the evaluation times and the results can be seen from the following table:

TABLE 3

(insects which damage plants)
*Phaedon* larvae test

| Active compounds | | Active compound concentration in % | Degree of destruction in % after 3 days |
|---|---|---|---|
| 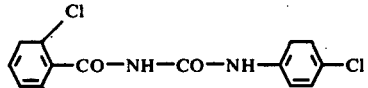<br>(known) | (A) | 0.1<br>0.01<br>0.001 | 100<br>55<br>0 |
| 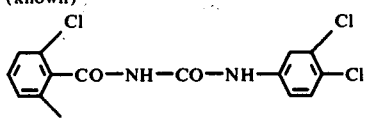<br>(known) | (B) | 0.1<br>0.01<br>0.001 | 100<br>15<br>0 |
| 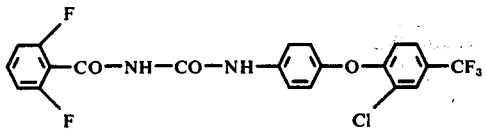 | (2) | 0.1<br>0.01<br>0.001 | 100<br>100<br>80 |
| 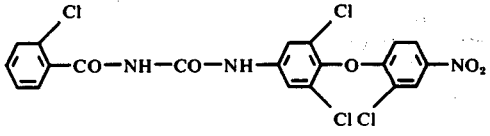 | (4) | 0.1<br>0.01<br>0.001 | 100<br>100<br>50 |
| 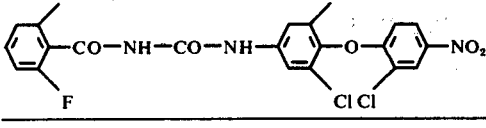 | (11) | 0.1<br>0.01<br>0.001 | 100<br>100<br>80 |

The process of the present invention is illustrated by the following preparative Examples.

EXAMPLE 4

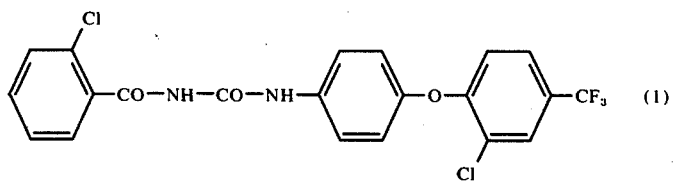

A solution of 3.7 g (0.02 mole) of 2-chlorobenzoylisocyanate in 20 ml of toluene was added dropwise at 80° C to 5.8 g (0.02 mole) of 4-(2'-chloro-4'-trifluoromethylphenoxy)-aniline in 100 ml of toluene. The batch was stirred for 1 hour at 80° C. After cooling, the product which had precipitated was filtered off and washed first with toluene and then with petroleum ether. After drying, 6.6 g (70% of theory) of analytically pure 2-chloro-4-trifluoromethyl-4'-[N-(N'-(o-chlorobenzoyl))-ureido]-diphenyl ether of melting point 182° C were obtained.

EXAMPLE 5

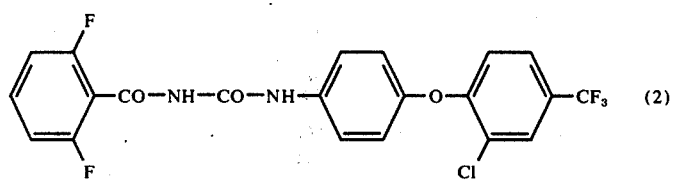

A solution of 3.7 g (0.02 mole) of 2,6-difluorobenzoylisocyanate in 20 ml of toluene was added dropwise at 80° C to a solution of 5.8 g (0.02 mole) of 4-(2'-chloro-4'-trifluoromethylphenoxy)-aniline in 100 ml of toluene. The batch was stirred for 1 hour at 80° C. The substance which separated out was filtered off after cooling the reaction mixture to 20° C and was washed with toluene and petroleum ether. After drying, 8 g (95% of theory) of 2-chloro-4-trifluoromethyl-4'-[N-(N'-(2,6-difluorobenzoyl))-ureido]-diphenyl ether of melting point 187° C were obtained.

EXAMPLE 6

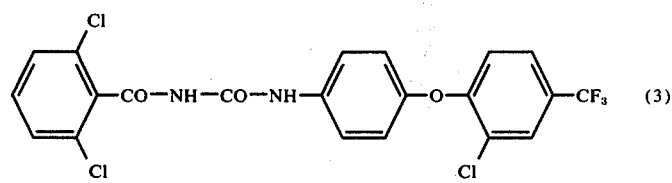

Using an analogous procedure to that described in Examples 4 and 5, 2-chloro-4-trifluoromethyl-4'-[N-(N'-(2,6-dichlorobenzoyl))-ureido]-diphenyl ether was obtained in a yield of 89% of theory, and with a melting point of 177° C.

EXAMPLE 7

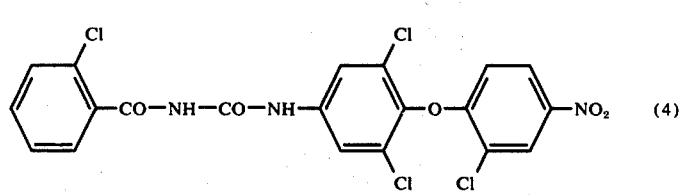

A solution of 2.8 g (0.015 mole) of 2-chlorobenzoylisocyanate in 10 ml of toluene was added dropwise at 80° C to 5 g (0.015 mole) of 3,5-dichloro-4-(2'-chloro-4'-nitrophenoxy)-aniline in 50 ml of toluene. The batch was stirred for 1 hour at 80° C. After cooling, the product which had precipitated was filtered off and was washed first with toluene and then with petroleum ether. After drying, 6.5 g (84% of theory) of analytically pure 2-chloro-4-nitro-2',6'-dichloro-4'-[N-(N'-(o-chlorobenzoyl))-ureido]-diphenyl ether of melting point 221° C were obtained.

EXAMPLE 8

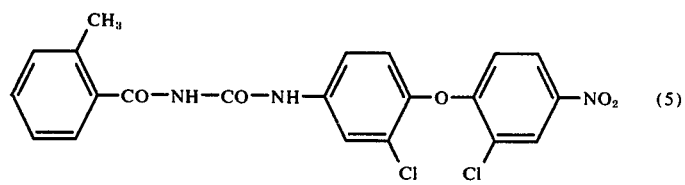

(5)

A solution of 3.25 g (0.02 mole) of 2-methyl-benzoylisocyanate in 20 ml of toluene was added dropwise at 80° C to a solution of 6.0 g (0.02 mole) of 3-chloro-4-(2'-chloro-4'-nitrophenoxy)-aniline in 80 ml of toluene. The batch was stirred for 1 hour at 80° C. The substance which separated out was filtered off after cooling the reaction mixture to 20° C and was washed with toluene and petroleum ether. After drying, 8 g (87% of theory) of 2-chloro-4-nitro-2'-chloro-4'-[N-(N'-(o-methylbenzoyl))-ureido]-diphenyl ether of melting point 220° C were obtained.

The following compounds were obtained by methods analogous to those described above.

| Compound No. | Formula | Yield (% of theory) | Physical data (melting point, ° C) |
|---|---|---|---|
| (6) | ![structure] | 94 | 223 |
| (7) | ![structure] | 82 | 208 |
| (8) | ![structure] | 87 | 227 |
| (9) | ![structure] | 83 | 201 |
| (10) | ![structure] | 87 | 206 |
| (11) | ![structure] | 96 | 235 |
| (12) | ![structure] | 70 | 220 |

EXAMPLE 9

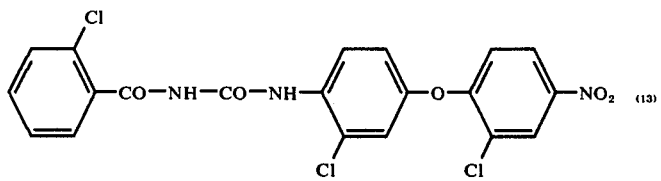

(13)

A solution of 3.7 g (0.02 mole) of 2-chlorobenzoylisocyanate in 20 ml of toluene was added dropwise at 30° C to 6.0 g (0.02 mole) of 4-(2'-chloro-4'-nitrophenoxy)-2-chloroaniline in 100 ml of toluene. The batch was stirred for 1 hour at 50° C. After cooling, the product which had precipitated was filtered off and was washed first with toluene and then with petroleum ether. After drying, 6.0 g (62% of theory) of analytically pure 2,3'-dichloro-4-nitro-4'-[N-(N'-(o-chlorobenzoyl))-ureido]-diphenyl ether of melting point 193° C were obtained.

EXAMPLE 10

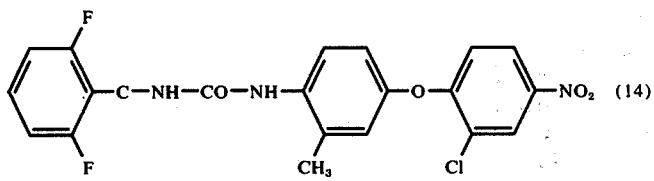

A solution of 3.7 g (0.02 mole) of 2,6-difluorobenzoylisocyanate in 20 ml of toluene was added dropwise at 50° C to a solution of 5.6 g (0.02 mole) of 4-(2'-chloro-4'-nitrophenoxy)-2-methylaniline in 100 ml of toluene. The batch was stirred for 1 hour at 60° C. The substance which separated out was filtered off after cooling the reaction mixture to 20° C and was washed with toluene and petroleum ether. After drying, 7 g (75% of theory) of 2-chloro-4-nitro-3'-methyl-4'-[N-(N'-2,6-difluorobenzoyl))-ureido]-diphenyl ether of melting point 190° C were obtained.

The following compounds were obtained by using an analogous procedure to that described in Examples 9 and 10:

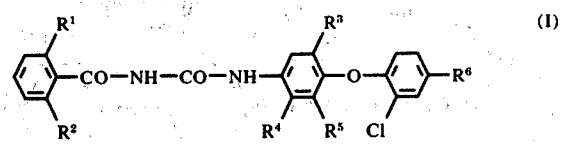

in which
R¹ is fluorine, chlorine, bromine or methyl,
R² is hydrogen, fluorine or chlorine,
R³ is hydrogen or chlorine,
R⁴ is hydrogen, chlorine or methyl,
R⁵ is hydrogen or chlorine and
R⁶ is nitro or trifluoromethyl.

2. A 2-chloro-4'-[N-(N'-benzoyl)-ureido]-diphenyl ether according to claim 1, in which R¹ is chlorine or fluorine, R² is hydrogen, chlorine or fluorine, R³, R⁴ and R⁵ each is hydrogen, and R⁶ is trifluoromethyl.

3. A 2-chloro-4'-[N-(N'-benzoyl)-ureido]-diphenyl

| No. | Formula | Physical data (melting point, ° C) | Yield (% of theory) |
|---|---|---|---|
| (15) | [F, F-phenyl-CO-NH-CO-NH-(Cl-phenyl)-O-(Cl-phenyl)-NO₂] | 200 | 93 |
| (16) | [Br-phenyl-CO-NH-CO-NH-(Cl-phenyl)-O-(Cl-phenyl)-NO₂] | 193 | 82 |
| (17) | [Cl-phenyl-CO-NH-CO-NH-(CH₃-phenyl)-O-(Cl-phenyl)-NO₂] | 197 | 65 |
| (18) | [Br-phenyl-CO-NH-CO-NH-(CH₃-phenyl)-O-(Cl-phenyl)-NO₂] | 200 | 86 |

It will be appreciated that the instant specification and examples are set forth by way of illustration and not limitation, and that various modifications and changes may be made without departing from the spirit and scope of the present invention.

What is claimed is:

1. A 2-chloro-4'-[N-(N'-benzoyl)-ureido]-diphenyl ether of the formula ether according to claim 1, in which R¹ is chlorine, fluorine or methyl, R² is hydrogen, chlorine or fluorine, R³ is hydrogen or chlorine, R⁴ is hydrogen, R⁵ is hydrogen or chlorine, and R⁶ is nitro.

4. A 2-chloro-4'-[N-(N'-benzoyl)-ureido]-diphenyl ether according to claim 1, in which R¹ is chlorine, fluorine or bromine, R² is hydrogen or fluorine, R³ is hydrogen, R⁴ is methyl or chlorine, R⁵ is hydrogen and R⁶ is nitro.

5. The compound according to claim 1 wherein such compound is 2-chloro-4-trifluoromethyl-4'-[N-(N'-(o-chlorobenzoyl))-ureido]-diphenyl ether of the formula

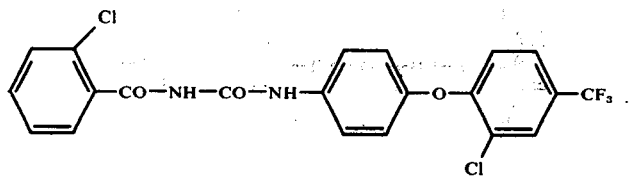

6. The compound according to claim 1 wherein such compound is 2-chloro-4-trifluoromethyl-4'-[N-(N'-2,6-difluorobenzoyl))-ureido]-diphenyl ether of the formula

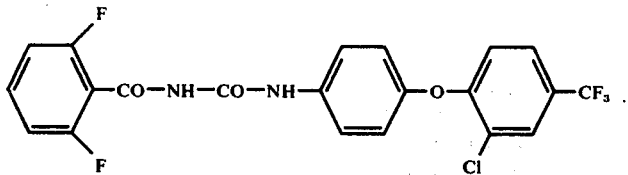

7. The compound according to claim 1 wherein such compound is 2-chloro-4-nitro-2',6'-dichloro-4'-[N-(N'-(o-chlorobenzoyl))-ureido]-diphenyl ether of the formula

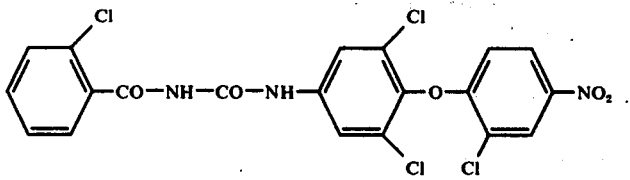

8. The compound according to claim 1 wherein such compound is 2-chloro-4-nitro-2',6'-dichloro-4'-[N-(N'-(2,6-difluorobenzoyl))-ureido]-diphenyl ether of the formula

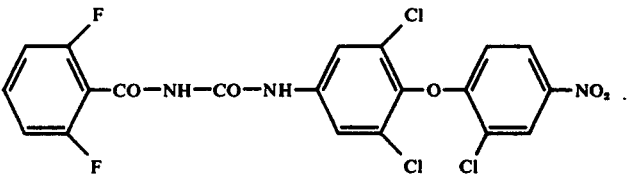

9. The compound according to claim 1 wherein such compound is 2-chloro-4-nitro-3'-methyl-4'-[N-(N'-(2,6-difluorobenzoyl)-ureido]-diphenyl ether of the formula

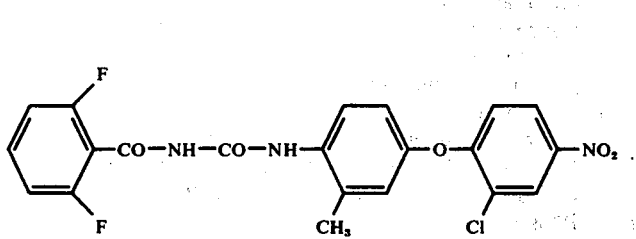

10. An insecticidal composition containing as active ingredient an insecticidally effective amount of a compound according to claim 1 in admixture with a diluent.

11. A method of combating insects which comprises applying to the insects or an insect habitat an insecticidally effective amount of a compound according to claim 1.

12. The method according to claim 11 in which said compound is
2-chloro-4-trifluoromethyl-4'-[N-(N'-(o-chlorobenzoyl))-ureido]-diphenyl ether,
2-chloro-4-trifluoromethyl-4'-[N-(N'-2,6-difluorobenzoyl))-ureido]-diphenyl ether,
2-chloro-4-nitro-2',6'-dichloro-4'-[N-(N'-(o-chlorobenzoyl))-ureido]-diphenyl ether,
2-chloro-4-nitro-2',6'-dichloro-4'-[N-(N'-(2,6-difluorobenzoyl))-ureido]-diphenyl ether or
2-chloro-4-nitro-3'-methyl-4'-[N-(N'-2,6-difluorobenzoyl))-ureido]-diphenyl ether.

* * * * *

UNITED STATES PATENT AND TRADEMARK OFFICE
CERTIFICATE OF CORRECTION

PATENT NO. : 4,005,223     Page 1 of 3
DATED : January 25, 1977
INVENTOR(S) : Wilhelm Sirrenberg, et al.

It is certified that error appears in the above-identified patent and that said Letters Patent are hereby corrected as shown below:

Col. 9 & 10,     After formula "(4)", under the
   Table 1 - continued     appropriate headings, add the following omitted data:

| Structure | No. | Conc. | % |
|---|---|---|---|
| 2,6-diCl-C$_6$H$_3$-CO-NH-CO-NH-C$_6$H$_2$(2,6-diCl)-O-C$_6$H$_4$-NO$_2$ | (8) | 0.1 / 0.01 / 0.001 | 100 / 100 / 100 |
| 2-F-C$_6$H$_4$-CO-NH-CO-NH-C$_6$H$_2$(2,6-diCl)-O-C$_6$H$_4$-NO$_2$ | (10) | 0.1 / 0.01 / 0.001 | 100 / 100 / 100 |
| 2,6-diF-C$_6$H$_3$-CO-NH-CO-NH-C$_6$H$_2$(2,6-diCl)-O-C$_6$H$_4$-NO$_2$ | (11) | 0.1 / 0.01 / 0.001 | 100 / 100 / 100 |
| 2-Cl-C$_6$H$_4$-CO-NH-CO-NH-C$_6$H$_3$(CH$_3$)-O-C$_6$H$_3$(Cl)-NO$_2$ | (17) | 0.1 / 0.01 / 0.001 | 100 / 100 / 100 |

UNITED STATES PATENT OFFICE
CERTIFICATE OF CORRECTION

Patent No. 4,005,223   Dated January 25, 1977

Inventor(s) Wilhelm Sirrenberg et al

It is certified that error appears in the above-identified patent and that said Letters Patent are hereby corrected as shown below:

Column 9 & 10

Table 1 - continued

Continuing, after formula (17) and under the appropriate headings, add the following omitted data:

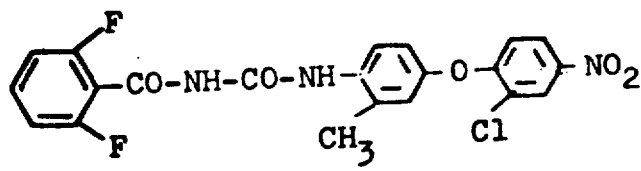

| | | |
|---|---|---|
| (14) | 0.1 | 100 |
| | 0.01 | 100 |
| | 0.001 | 100 |
| (18) | 0.1 | 100 |
| | 0.01 | 100 |
| | 0.001 | 100 |
| (13) | 0.1 | 100 |
| | 0.01 | 100 |
| | 0.001 | 100 |
| (15) | 0.1 | 100 |
| | 0.01 | 100 |
| | 0.001 | 100 |

UNITED STATES PATENT OFFICE
CERTIFICATE OF CORRECTION

Patent No. 4,005,223     Dated January 25, 1977

Inventor(s) Wilhelm Sirrenberg et al

It is certified that error appears in the above-identified patent and that said Letters Patent are hereby corrected as shown below:

Column 9 & 10

Table 1 - continued

Continuing, after formula (17) and under the appropriate headings, add the following omitted data:

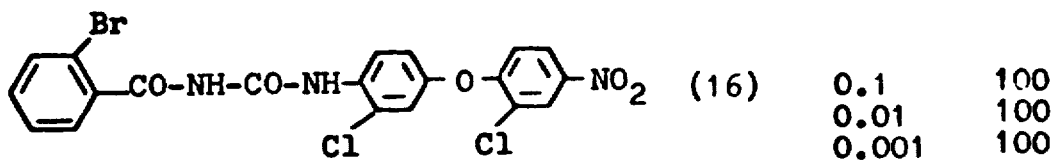

(16)    0.1     100
       0.01    100
       0.001   100

Signed and Sealed this twenty-third Day of August 1977

[SEAL]

Attest:

RUTH C. MASON
Attesting Officer

C. MARSHALL DANN
Commissioner of Patents and Trademarks